(12) United States Patent
Motoyashiki et al.

(10) Patent No.: US 6,200,595 B1
(45) Date of Patent: Mar. 13, 2001

(54) MEDICAL ADHESIVE

(75) Inventors: Yukiko Motoyashiki; Hideaki Yamada, both of Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/296,541

(22) Filed: Apr. 22, 1999

(30) Foreign Application Priority Data

Apr. 24, 1998 (JP) .................................................. 10-114520

(51) Int. Cl.$^7$ ...................................................... A61L 15/00
(52) U.S. Cl. .......................... 424/445; 424/443; 424/444
(58) Field of Search ................................... 424/443, 444, 424/445, 446, 447, 448, 449

(56) References Cited

U.S. PATENT DOCUMENTS

| | | | |
|---|---|---|---|
| 3,878,086 | * 4/1975 | Haswell et al. | 204/635 |
| 4,740,534 | 4/1988 | Matsuda et al. | 523/111 |
| 4,806,614 | 2/1989 | Matsuda et al. | 528/59 |
| 4,952,618 | * 8/1990 | Olsen | 524/17 |
| 5,429,591 | * 7/1995 | Yamamoto et al. | 602/54 |

FOREIGN PATENT DOCUMENTS

| | | |
|---|---|---|
| 53-110693 | 9/1978 | (JP) . |
| 61-73665 | 4/1986 | (JP) . |
| 3-287538 | 12/1991 | (JP) . |
| 8-224293 | 9/1996 | (JP) . |

* cited by examiner

Primary Examiner—Michael A. Williamson
(74) Attorney, Agent, or Firm—Oblon, Spivak, McClelland, Maier & Neustadt, P.C.

(57) ABSTRACT

A medical adhesive which comprises a polyion complex film formed from a polycationic substance and a polyanionic substance. This medical adhesive provides a sufficient gel strength for adhesion of tissues, and it is superior in handling properties and safety for the living body.

14 Claims, No Drawings

MEDICAL ADHESIVE

BACKGROUND OF THE INVENTION

1. Field of the Invention

The present invention relates to a medical adhesive which comprises a polyion complex film formed from a polycationic substance and a polyanionic substance. The medical adhesive of the present invention, which is in the form of film, absorbs blood or exudate from living tissues at the affected part and sticks to the tissue surface as it gels. It is particularly suitable for use as a tissue adhesive for surgical operations.

2. Discussion of the Background

Conventional tissue adhesives for surgical operations are illustrated below.

A typical one is so-called fibrin glue composed of fibrinogen, blood coagulation factor XIII, and thrombin. It is commercially available from several producers. Containing fibrinogen derived from human plasma, it has a disadvantage of being possibly infected with pathogenic organisms. In addition, it necessitates a step of mixing several materials immediately before use. This is troublesome.

Another one is cyanoacrylate-based tissue adhesive, which is also commercially available. It cures fast and provides high bond strength, but it has a disadvantage of evolving harmful formaldehyde upon decomposition in the living body.

A new product in the Japanese market is a tissue adhesive composed of gelatin, resorcinol, and formaldehyde. It also poses a problem with toxicity due to formaldehyde. In addition, it necessitates a step of mixing several reagents immediately before use. This is troublesome.

A tissue adhesive based on diisocyanate-urethane prepolymer is disclosed in Japanese Patent Laid-open No. 290465/1985, U.S. Pat. No. 4740534, and U.S. Pat. No. 4806614. It has not yet been put to practical use because it evolves, upon decomposition, diisocyanate which may be carcinogenic.

Conventional tissue adhesives shown above have many problems with biological safety (e.g., infection, sensitization, and toxicity) and handling properties.

In the meantime, it is well known that a polyion complex is formed rapidly when a polycationic substance and a polyanionic substance are mixed together in the presence of water. The polyion complex finds use in many application areas including drugs and medical instruments. An example of it is a polymeric composite material obtained by reaction between an anionic partial substitution product of dextran and a cationic partial substitution product of polysaccharide, which is used as a hemostatic in the form of powder, granules, or tablets, as disclosed in Japanese Patent Laid-open No. 110693/1978. Another example is aqueous solutions of polyanionic material and polycationic material (containing a calcium salt solution) which form a wound protecting layer when sprayed together on a wound, as disclosed in Japanese Patent Laid-open No. 73665/1986. The above-mentioned conventional polyion complex is applied in the form of powder or formed in situ on the wound from two solutions mixed together. On gelation, it merely gives rise to a gel which is not strong enough to be used as a tissue adhesive.

Another application of the polyion complex is in the active ingredient of an agent to promote regeneration of periodontal tissues by injection into periodontal pockets, as disclosed in Japanese Patent Laid-open No. 287538/1991. However, nothing is disclosed about use as a tissue adhesive.

A multilayered body for wound treatment is disclosed in Japanese Patent Laid-open No. 224293/1996. It is composed of chitosan, alginic acid, and chitin which are arranged one over another on a substrate. It is produced by coating the substrate with chitin (or chitin dispersion) and then with a previously prepared chitosan-alginic acid complex, and finally drying the thus formed laminate. Since chitosan and alginic acid are not dissolved in water when they are made into a complex, they do not form a polyion complex in the multilayer body for wound treatment.

SUMMARY OF THE INVENTION

It is an object of the present invention to provide a medical adhesive which, after application to an affected part, absorbs blood or tissue exudate from the affected part, thereby turning into a gel which sticks to the affected part and firmly bonds tissues together.

It is another object of the present invention to provide an easy-to-use medical adhesive which dispenses with such pretreatment as mixing and dissolution during operations.

It is further another object of the present invention to provide a medical adhesive which is safe for the living body without possibility of infection and sensitization.

After their intensive studies, the present inventors found that the above-mentioned objects are achieved by a medical adhesive which comprises a polyion complex film formed from a polycationic substance and a polyanionic substance. The present invention was completed on the basis of this finding.

DETAILED DESCRIPTION OF THE PREFERRED EMBODIMENTS

The polycationic substance used in the present invention is not specifically restricted so long as it meets the requirement that it have a plurality of cationic groups in the molecule so as to form a gel-like polyion complex with the polyanionic substance (explained later) in the presence of water, with the polyion complex functioning as an adhesive for living tissues, causing little harmful reaction to the living body. It should preferably be one which is decomposed and absorbed by the living body after the affected part has healed.

Another condition for the polycationic substance is that it have sufficient hydrophilic groups to dissolve or swell in water and be positively charged in water due to its cationic groups formed by dissociation.

Examples of the cationic group include amino group, monoalkylamino groups (such as methylamino group, and ethylamino group), dialykylamino groups (such as dimethylamino group and diethylamino-group), imino groups, and guanidino groups. The polycationic substance should preferably contain more than one amino group in its molecule.

Any known polycationic substance may be used in the present invention. Preferred examples include basic polysaccharides (such as chitosan and aminated cellulose), homopolymers or co-polymers of basic amino acids (such as polylysine, polyarginine, and lysine-arginine copolymer), basic vinyl polymers (such as polyvinylamine and polyallylamine), and their salts (such as hydrochloride and acetate). Of these examples, basic polysaccharides and their derivatives (such as acetylated products) and salts are particularly preferable. A preferred example of the basic polysaccharides is chitosan. Chitosan is a deacetylation product of chitin. For chitosan to have good water solubility and an ability to be absorbed by the living body, its degree of deacetylation should be in the range of 40–100%, preferably 45–90%, more preferably 50–80%.

The polycationic substance may be used in its crosslinked form. If it has amino groups, it may be crosslinked by condensation of the amino groups with a dicarboxylic acid. Any other known methods may be used for crosslinking.

The polycationic substance is not specifically restricted in molecular weight. However, it should have a molecular weight such that its 1% aqueous solution at 20° C. has a viscosity of 10,000 cp or lower, preferably 5,000 cp or lower. This viscosity increases accordingly as the molecular weight increases. With a higher viscosity, the solution is difficult to cast into film, and the resulting film becomes hard when dried and is poor in ability to be absorbed by the living body.

The polycationic substance that can be used in the invention may be a low-molecular weight diamine or polyamine. They include, for example, diaminoalkanes having 2 amino groups in one molecule (such as diaminoethane, diaminopropane, diaminobutane, diaminopentane, and diaminohexane), mono- or dilysylaminoalkanes having 3–4 amino groups in one molecule (such as N-(lysyl)-diaminoethane, N,N'-(dilysyl)-diaminoethane, N-(lysyl)-diaminohexane, and N,N'-(dilysyl)-diaminohexane), and those compounds having 5 or more amino groups in one molecule.

More than one kind of polycationic substance may be used for the medical adhesive of the present invention.

The polyanionic substance used in the present invention is not specifically restricted so long as it meets the requirement that it have a plurality of anionic groups in the molecule so as to form a gel-like polyion complex with the polycationic substance (explained above) in the presence of water, with the polyion complex functioning as an adhesive for living tissues, causing little harmful reaction to the living body. It should preferably be one which is decomposed and absorbed by the living body after the affected part has healed.

Another condition for the polyanionic substance is that it have sufficient hydrophilic groups to dissolve or swell in water and be negatively charged in water due to its anionic groups formed by dissociation.

The anionic group includes, for example, carboxyl group, sulfate group, sulfonate group, and phosphate group. A preferred polyanionic substance is one which has more than one carboxyl group in one molecule.

Preferred examples of the polyanionic substance used in the present invention are given below.

Natural acidic polysaccharides and their derivatives, such as alginic acid, hyaluronic acid, chondroitin sulfate, dextran sulfate, and pectin, which have anionic groups such as carboxyl group and sulfate group.

Acidic polysaccharides artificially synthesized by combining a polysaccharide (e.g., cellulose, dextran, and starch, which originally do not have anionic groups, e.g., carboxyl group and sulfate group) with anionic groups, such as carboxymethylcellulose, carboxymethyldextran, sulfated cellulose, and sulfated dextran, and their derivatives.

Homopolymers or copolymers of acidic amino acids, such as polyglutamic acid, polyasparagic acid, and glutamic acid-asparagic acid copolymer.

Acidic vinyl polymers such as polyacrylic acid and their salts (sodium salt and potassium salt).

The polyanionic substance may be used in its crosslinked form. If it has carboxyl groups, it may be crosslinked by condensation of the carboxyl groups with a diamine. Any other known methods may be used for crosslinking.

Examples of the derivatives of acidic polysaccharides include those which are formed by reacting all or part of their hydroxyl groups with acetic acid, nitric acid, sulfuric acid, or phosphoric acid, and those which are formed by esterifying all or part of their carboxyl groups with a low-molecular weight alcohol such as ethylene glycol and propylene glycol. Their typical examples are ethylene glycol ester of alginic acid, propylene glycol ester of alginic acid, ethylene glycol ester of hyaluronic acid, and propylene glycol ester of hyaluronic acid. These derivatives are not specifically restricted in the degree of esterification. However, the degree of esterification should preferably be 80% or less, more preferably 30% or less. An excessively high degree of esterification leads to a decrease in the ratio of carboxyl groups or a decrease in anionicity, which in turn leads to a polyion complex (formed from the polyanionic substance and the polycationic substance) low in mechanical strength.

Examples of the salts of the acidic polysaccharides and their derivatives include salts with monovalent ions, such as alkali metal salts (sodium salts and potassium salts) and ammonium salts.

Preferred examples of the polyanionic substance include acidic polysaccharides, derivatives thereof, and salts thereof, particularly alginic acid and derivative thereof (e.g., propylene glycol ester of alginic acid) and salts thereof (e.g., alkali metal salts such as sodium salts).

The polyanionic substance is not specifically restricted in molecular weight. However, it should have a molecular weight such that its 1% aqueous solution at 20° C. has a viscosity of 10,000 cp or lower, preferably 5,000 cp or lower. This viscosity increases accordingly as the molecular weight increases. With a higher viscosity, the solution is difficult to cast into film, and the resulting film becomes hard when dried and is poor in ability to be absorbed by the living body.

The polyanionic substance that can be used in the invention may be a low-molecular weight compound having more than one anionic group in one molecule. Examples of such a compound include succinic acid and malonic acid, which have 2 carboxyl groups in one molecule.

More than one kind of polyanionic substance may be used for the medical adhesive of the present invention.

In the present invention, any polycationic substance may be combined with any polyanionic substance so long as they form a polyion complex capable of gelation when mixed together in the presence of water. However, from the standpoint of safety, at least one of them should preferably be a bioabsorbable polymer.

The polycationic substance and the polyanionic substance may be mixed together in any ratio so long as they form a polyion complex capable of gelation when mixed together in the presence of water. One of them may be used in an excess amount relative to the other.

The medical adhesive of the present invention is obtained in the form of film when a polyion complex cast into a thin layer is dried. The procedure may be accomplished in several ways as follows.

The polycationic substance and the polyanionic substance are dissolved separately in water or any solvent, and the resulting solutions are mixed together and the mixture is cast into a thin layer, or the resulting solutions are mixed together while being cast simultaneously into a thin layer, or one solution is cast into a thin layer and then the other solution is cast thereon for mixing.

Either of the polycationic substance or the polyanionic substance is dissolved in water or any solvent, and the resulting solution is cast into a thin film while dissolving the other therein or the resulting solution is cast into a thin film and the other is subsequently added thereto, or in the resulting solution is dissolved the other and the thus obtained solution is cast into a thin layer.

The polycationic substance and the polyanionic substance are mixed together in the form of powder and the resulting mixture is dissolved in water or any solvent and the resulting solution is cast into a thin layer. Alternatively, they are dissolved in water or any solvent and simultaneously cast into a thin layer. Or, the powder mixture is sprayed to form a thin layer, which is given water or any solvent for dissolution.

Either of the polycationic substance or the polyanionic substance is pulverized and the other is made into a dry film, and the powder is spread over the film and then given water or any solvent for dissolution.

The polyion complex cast into a thin layer may be dried in any way so long as the polycationic substance, the polyanionic substance, and the polyion complex are not degraded. Typical drying methods include natural drying, vacuum drying, solvent substitution drying, heat drying, and draft drying.

The medical adhesive of the present invention will be improved in tissue bonding ability if the polycationic substance or the polyanionic substance constituting the polyion complex has a tissue bonding ability by itself and either of them is present in a larger amount than the other on one side of the film.

In the case where the medical adhesive is formed by laminating films of polyion complex on top of the other, it is desirable that the moiety derived from the polycationic substance abounds on one side of the film and the moiety derived from the polyanionic substance abounds on the other side of the film. In this way it is possible to produce good bonding between the laminated films.

The polyion complex film as mentioned above may be produced by any method as shown below.

The polycationic substance and the polyanionic substance are dissolved separately in water or any solvent. One solution is cast into a thin layer and the other solution is cast into a thin layer thereon, and the resulting laminate is dried afterwards.

Either the polycationic substance or the polyanionic substance is made into a dry film and the other is dissolved in water or any solvent. The resulting solution is applied to the dry film and then dried.

Either the polycationic substance or the polyanionic substance is dissolved in water or any solvent, and the resulting solution is cast into a thin layer. The other is dispersed on the thin layer for dissolution, followed by drying.

The polycationic substance and the polyanionic substance are separately made into dry films and the films in laminated state are dissolved in water or any solvent.

The solvent employed in the above-mentioned methods is not specifically restricted so long as it dissolves the polycationic substance and the polyanionic substance. Water or an aqueous solution of an inorganic salt is adequate because of its ability to sufficiently charge the polycationic substance and the polyanionic substance. The concentration of the polycationic substance and the polyanionic substance in the solution is not specifically restricted. It may be properly adjusted according to each individual method employed.

In the case where at least one of the polycationic substance or the polyanionic substance is a salt which decreases in solubility in water when the counter ion of the cationic group or anionic group is removed, it is desirable to form the polyion complex film first and then remove the counter ion from the film. In this way it is possible to improve the medical adhesive in mechanical strength.

One way to remove the counter ions of cationic groups from the polyion complex film is by dipping in an alkaline aqueous solution of a base such as sodium hydroxide, potassium hydroxide, sodium hydrogen carbonate, and ammonia, followed by rinsing with an adequate solvent and drying. One way to remove the counter ions of anionic groups from the polyion complex film is by dipping in an acidic aqueous solution of an acid such as hydrochloric acid, sulfuric acid, acetic acid, phosphoric acid, citric acid, malic acid, and tartaric acid, followed by rinsing with an adequate solvent and drying. The rinsing solvent is not specifically restricted so long as it does not dissolve but wets the polyion complex film. Preferred solvents include water and aqueous solutions of inorganic salts (such as sodium chloride, calcium chloride, and sodium acetate) which effectively dissolve the counter ion in the film.

The above-mentioned alkaline and acidic solutions and rinsing solvent may be incorporated with an organic solvent (such as ethanol, methanol, and acetone) so as to prevent the polyion complex film from swelling and hence decreasing in mechanical strength.

If the counter ion is highly volatile, it can be removed by heating the polyion complex film at a temperature not high enough to deteriorate the polycationic substance or the polyanionic substance constituting the polyion complex film.

The medical adhesive of the present invention may take on a laminated form composed of more than one polyion complex film so that it is improved in mechanical strength. The number of layers for lamination should be 2 to 15, preferably 2 to 10, so that the resulting laminate has good water absorption and flexibility in its dry state. It is also possible to laminate layers of more than one kind so that the resulting medical adhesive exhibits superior mechanical strength, tissue bonding ability, and ability to be absorbed by the living body which are characteristic of each polyion complex constituting the individual layer.

The medical adhesive in the laminate form of polyion complex films may be produced by placing films (which have been wetted with an adequate solvent) on top of the other, followed by drying. The solvent to wet the films is not specifically restricted so long as it does not dissolve but wets the polyion complex film. An adequate solvent is water or an aqueous solution of an inorganic salt which permits individual films to produce good adhesion due to electric charges. This solvent may be incorporated with an adequate polycationic substance or a polyanionic substance for adhesion between the surfaces of the laminated films. The solvent may also be incorporated with an organic solvent (such as ethanol, methanol, and acetone) so as to prevent the polyion complex film from swelling.

As mentioned above, the present invention provides a use of a polyion complex film formed from a polycationic substance and a polyanionic substance for the production of a medical adhesive.

The polyion complex film is not specifically restricted in thickness. It should be 0.5 mm or thinner, preferably 0.2 mm or thinner, so that it has good water absorption and flexibility in its dry state. In addition, it should contain water in an amount not more than 60%, preferably not more than 30%;

with an excessively high water content, it decreases in water absorption when applied to the affected part.

The medical adhesive of the present invention will find use particularly as a tissue adhesive for surgical operations. For example, it is used for adhesion of a skin; adhesion of a section of the organ (such as liver and spleen); anastomosis of the intestine and the salpinx; adhesion of the dura mater, pleura, fascia, peritoneum, etc.; hemostasis of bleeding from the organ; hemostasis of suture (to prevent bleeding through stitches); and prevention of air leak from the lung.

The medical adhesive of the present invention may be used in any way so long as it absorbs water (blood and tissue fluids) for gelation after it has been applied to the affected part. For example, it may be applied, in its dry state, to the affected part which needs adhesion, so that it is allowed to absorb water (blood and tissue fluids) from the affected part and to become a gel.

If the affected part does not have sufficient water for gelation, it is possible to promote gelation by supplying water externally after the medical adhesive has been applied to the affected part. The water to be supplied externally is not specifically restricted so long as it is not harmful to the affected part. Physiological saline solution or Ringer solution is adequate.

As mentioned above, the present invention provides a method for bonding the living tissues together by application to the affected part of a polyion complex film formed from a polycationic substance and a polyanionic substance. Also, the present invention provides the use of a polyion complex film formed from a polycationic substance and a polyanionic substance to bond the living tissues together.

The present invention provides a medical adhesive which, after application to the affected part, absorbs blood or exudate from the affected part to become a gel and strongly adheres to the tissue.

The medical adhesive of the present invention gels as soon as it adheres to the tissues of the affected part and hence it can be used easily and effectively. It strongly adheres to the tissues and is safe for the living body without possibility of infection and sensitization.

Moreover, the medical adhesive of the present invention is in the form of polyion complex film which gels upon contact with the tissue fluid of the affected part. Therefore, it is easy to handle without requiring pretreatment (such as mixing and dissolution) when it is used as a tissue adhesive during operation.

EXAMPLES

The invention will be described in more detail with reference to the following examples, which are not intended to restrict the scope of the invention.

Example 1

In 100 ml of 0.1 N hydrochloric acid was dissolved 1 g of polyallylamine (L-type, having a molecular weight of 10,000, from Nitto Boseki Co., Ltd.). The resulting solution was designated as Solution 1. In 100 ml of distilled water was dissolved 1 g of sodium alginate (having a viscosity of 100–150 cp, from Wako Pure Chemical Industries, Ltd.). The resulting solution was designated as Solution 2. All of Solution 1 and all of Solution 2 were mixed together on a glass plate, and the mixture was cast into a thin layer. The thin layer was air-dried. The dried film was wetted with distilled water, and 3 pieces of the wetted film were placed one over another. The resulting laminate was air-dried again. After drying, the laminated film was peeled off from the glass plate and tested according to the procedure shown in the test example. The results are shown in Table 1.

Example 2

In 100 ml of 0.1 N acetic acid was dissolved 1 g of chitosan (chitosan 500 with a degree of deacetylation of 85%, from Wako Pure Chemical Industries, Ltd.). The resulting solution was designated as Solution 1. In 100 ml of distilled water was dissolved 1 g of sodium alginate (having a viscosity of 500–600 cp, from Wako Pure Chemical Industries, Ltd.). The resulting solution was designated as Solution 2. All of Solution 1 and all of Solution 2 were mixed together on a glass plate, and the mixture was cast into a thin layer. After draft drying, the resulting film was peeled off from the glass plate and tested according to the procedure shown in the test example. The results are shown in Table 1.

Example 3

In 100 ml of 0.1 N acetic acid was dissolved 1 g of chitosan (chitosan 500 with a degree of deacetylation of 85%, from Wako Pure Chemical Industries, Ltd.). The resulting solution was designated as Solution 1. In 100 ml of distilled water was dissolved 1 g of sodium alginate (having a viscosity of 300–400 cp, from Wako Pure Chemical Industries, Ltd.). The resulting solution was designated as Solution 2. All of Solution 1 and all of Solution 2 were mixed together on a glass plate, and the mixture was cast into a thin layer. After draft drying, the dried film was wetted with distilled water, and 5 pieces of the wetted film were placed one over another. The resulting laminate was draft-dried again. After drying, the laminated film was peeled off from the glass plate and tested according to the procedure shown in the test example. The results are shown in Table 1.

Example 4

In 100 ml of 0.1 N acetic acid was dissolved 1 g of chitosan (chitosan 500 with a degree of deacetylation of 85%, from Wako Pure Chemical Industries, Ltd.). The resulting solution was designated as Solution 1. In 100 ml of distilled water was dissolved 1 g of sodium dextran sulfate (having a molecular weight of 500,000, from Wako Pure-Chemical Industries, Ltd.). The resulting solution was designated as Solution 2. All of Solution 1 and all of Solution 2 were mixed together on a glass plate, and the mixture was cast into a thin layer, followed by heat-drying at 40° C. The dried film was wetted with distilled water, and 5 pieces of the wetted film were placed one over another. The resulting laminate was heat-dried again. After drying, the laminated film was peeled off from the glass plate and tested according to the procedure shown in the test example. The results are shown in Table 1.

Example 5

In 100 ml of 0.1 N acetic acid was dissolved 1 g of chitosan (chitosan 500 with a degree of deacetylation of 85%, from Wako Pure Chemical Industries, Ltd.). The resulting solution was designated as Solution 1. In 100 ml of distilled water was dissolved 1 g of sodium alginate (having a viscosity of 500–600 cp, from Wako Pure Chemical Industries, Ltd.). The resulting solution was designated as Solution 2. All of Solution 1 and all of Solution 2 were cast onto a glass plate such that the former formed the lower layer and the latter formed the upper layer, and the resulting laminated film was draft-dried. The dried film was wetted with distilled water, and 5 pieces of the wetted film were placed one over another. The resulting laminate was draft-dried again. After drying, the laminated film was peeled off from the glass plate and tested according to the procedure shown in the test example. The results are shown in Table 1.

Example 6

In 100 ml of 0.1 N acetic acid was dissolved 1 g of chitosan (chitosan 500 with a degree of deacetylation of 85%, from Wako Pure Chemical Industries, Ltd.). The resulting solution was designated as Solution 1. In 100 ml of distilled water was dissolved 1 g of sodium alginate (having a viscosity of 500–600 cp, from Wako Pure Chemical Industries, Ltd.). The resulting solution was designated as Solution 2. All of Solution 1 and all of Solution 2 were cast onto a glass plate such that the former formed the upper layer and the latter formed the lower layer, and the resulting laminated film was heat-dried at 40° C. The dried film, together with the glass plate, was dipped in 0.1 N sodium hydroxide 60% ethanol aqueous solution, followed by rinsing with 60% ethanol aqueous solution. After draft drying, the film was peeled off from the glass plate. That side of the film which abounds the moiety derived from the chitosan was tested according to the procedure shown in the test example. The results are shown in Table 1.

Example 7

In 100 ml of 0.1 N acetic acid was dissolved 1 g of chitosan (having a degree of deacetylation of 60% and a viscosity of 300–400 cp). The resulting solution was designated as Solution 1. In 100 ml of distilled water was dissolved 1 g of sodium alginate (having a viscosity of 500–600 cp, from Wako Pure Chemical Industries, Ltd.). The resulting solution was designated as Solution 2. All of Solution 1 and all of Solution 2 were cast onto a glass plate such that the former formed the upper layer and the latter formed the lower layer, and the resulting laminated film was heat-dried at 40° C. The dried film, together with the glass plate, was dipped in 0.1 N sodium hydroxide 60% ethanol aqueous solution, followed by rinsing with 60% ethanol aqueous solution. After draft drying, the film was peeled off from the glass plate. That side of the film which abounds the moiety derived from the chitosan was tested according to the procedure shown in the test example. The results are shown in Table 1.

Comparative Example 1

In 100 ml of 0.1 N hydrochloric acid was dissolved 1 g of polyallylamine (L-type, having a molecular weight of 10,000, from Nitto Boseki Co., Ltd.). The resulting solution was cast onto a glass plate. After air-drying, the film was peeled off from the glass plate and tested according to the procedure shown in the test example. The results are shown in Table 1.

Comparative Example 2

In 100 ml of distilled water was dissolved 2 g of sodium alginate (having a viscosity of 300–400cp, Wako Pure Chemical Industries, Ltd.). The resulting solution was cast onto a glass plate. After draft drying, the film was peeled off from the glass plate and tested according to the procedure shown in the test example. The results are shown in Table 1.

Comparative Example 3

In 100 ml of 0.1 N hydrochloric acid was dissolved 1 g of polyallylamine (L-type, having a molecular weight of 10,000, from Nitto Boseki Co., Ltd.). In 100 ml of distilled water was dissolved 2 g of sodium alginate (having a viscosity of 300–400cp, from Wako Pure Chemical Industries, Ltd.). The resulting two solutions were previously mixed together and the mixture was applied to the affected part. The effect was examined according the procedure shown in the test example. The results are shown in Table 1.

Comparative Example 4

In 100 ml of 0.1 N hydrochloric acid was dissolved 1 g of polyallylamine (L-type, having a molecular weight of 10,000, from Nitto Boseki Co., Ltd.). In 100 ml of distilled water was dissolved 2 g of sodium alginate (having a viscosity of 300–400cp, from Wako Pure Chemical Industries, Ltd.). The resulting two solutions were mixed together on the affected part at the time of application. The effect was examined according the procedure shown in the test example. The results are shown in Table 1.

Comparative Example 5

In 500 ml of water was dispersed 0.8 g of chitosan cotton (obtained by loosening nonwoven fabric). The resulting dispersion was spread uniformly over a piece of filter paper (30×25 cm) and filtered so that a chitosan layer was formed on the filter paper. On the chitosan layer was placed a piece of nonwoven fabric of alginic acid (1 mm thick) so that the former was transferred to the latter. The assembly was given dropwise 200 ml of water and then freeze-dried in a vacuum. Thus there was obtained a chitosan-alginic acid sheet. The chitosan side of this sheet was tested according the procedure shown in the test example. The results are shown in Table 1.

Comparative Example 6

Fibrin glue (from Bering Werke Co., Ltd.) was tested according the procedure shown in the test example. The results are shown in Table 1.

Comparative Example 7

In 100 ml of distilled water was dissolved 0.13 g of sodium dextran sulfate (having a molecular weight of 500,000, from Wako Pure Chemical Industries, Ltd.). The resulting solution was adjusted to pH 2.8 with hydrochloric acid. In 50 ml of distilled water was dissolved 0.05 g of chitosan (chitosan 500 from Wako Pure Chemical Industries, Ltd.). The resulting solution was adjusted to pH 2.6 with hydrochloric acid. The resulting two solutions were mixed together at room temperature for 30 minutes. The mixture was centrifuged to give a white precipitate. This precipitate was washed with water and vacuum-dried to give a white powder. This powder was sterilized by γ-rays (26 kGy). It was tested according the procedure shown in the test example. The results are shown in Table 1.

Test Example (Measurement of adhesion strength of incision wound in the skin)

The abdomen of an 8-week old mouse (ICR) was cut and an incision wound (1 cm long) was made in the peritoneum. To the incision wound was stuck the test piece (1×1.5 cm) obtained in Examples 1 to 7 or Comparative Examples 1, 2, or 5. (The test piece in Examples 5 to 7 was stuck such that the chitosan-rich side faced the wound; and the test piece in Comparative Example 5 was stuck such that the chitosan side faced the wound.) To the incision wound was also applied or sprayed the test piece obtained in Comparative Examples 3, 4, 6, or 7. Ten minutes later, the mouse was killed, and a rectangular section (1×2 cm) was cut out of the wound. Both ends of the section were tied up with a nylon thread. The section was pulled in the direction perpendicular to the bonded incision wound by using Autograph Model AGS-50A (from Shimadzu Corporation). The tensile strength measured when the incision wound separated was regarded as the adhesion strength. The adhesion strength per unit area of the section is shown in Table 1.

TABLE 1

| | Polycationic substance | Polyanionic substance | Remarks | Adhesion Strength (gf/cm$^2$) |
|---|---|---|---|---|
| Example 1 | Polyallylamine hydrochloride | Sodium alginate | 3-layer film | 22 |
| Example 2 | Chitosan acetate | Sodium alginate | Film | 20 |
| Example 3 | Chitosan acetate | Sodium alginate | 5-layer film | 46 |
| Example 4 | Chitosan acetate | Sodium dextran sulfate | 5-layer film | 54 |
| Example 5 | Chitosan acetate | Sodium alginate | 5-layer film, one side rich in chitosan | 69 |
| Example 6 | Chitosan acetate | Sodium alginate | Film, one side rich in chitosan, treated with NaOH solution | 66 |
| Example 7 | Chitosan acetate | Sodium alginate | Film, one side rich in chitosan, treated with NaOH solution | 51 |
| Comparative Example 1 | Polyallylamine hydrochloride | — | Film | Dissolved |
| Comparative Example 2 | — | Sodium alginate | Film | Dissolved |
| Comparative Example 3 | Polyallylamine hydrochloride | Sodium alginate | Applied after mixing with water | Dropped |
| Comparative Example 4 | Polyallylamine hydrochloride | Sodium alginate | Aqueous solutions were mixed in the affected part | Dropped |
| Comparative Example 5 | Chitosan cotton | Alginic acid nonwoven fabric | Composite sheet | 2 |
| Comparative Example 6 | — | — | Fibrin glue | 10 |
| Comparative Example 7 | Chitosan hydrochloride | Sodium dextran sulfate | Solutions were mixed and dried to give a powder | 4 |

It is apparent from Table 1 that all the samples in Examples 1 to 7 gave an adhesion strength at least 20 gf/cm$^2$, whereas the samples in Comparative Examples 1 and 2 dissolved immediately after application (and hence was unable to provide adhesion), the samples in Comparative Examples 3 and 4 dropped without adhesion, and the samples in Comparative Examples 5 to 7 merely provided poor adhesion of 2 gf/cm$^2$, 10 gf/cm$^2$ and 4 gf/cm$^2$ respectively.

The present application is based on Japanese Application 10-114520, filed Apr. 24, 1998, the entire disclosure of which is incorporated herein by reference.

What is claimed is:

1. A medical adhesive which comprises a polyion complex of a polycationic substance and a polyanionic substance formed into a film.

2. A medical adhesive according to claim 1, wherein the polycationic substance has more than one amino group in one molecule.

3. A medical adhesive according to claim 2, wherein the substance having more than one amino group in one molecule is a basic polysaccharide, a derivative thereof, or a salt thereof.

4. A medical adhesive according to claim 3, wherein said substance is chitosan, a derivative thereof, or a salt thereof.

5. A medical adhesive according to claim 1 wherein the polyanionic substance has more than one carboxyl group in one molecule.

6. A medical adhesive according to claim 5, wherein the substance having more than one carboxyl group in one molecule is an acidic polysaccharide, a derivative thereof, or a salt thereof.

7. A medical adhesive according to claim 6, wherein said substance is alginic acid, a derivative thereof, or a salt thereof.

8. A medical adhesive according to claim 1 wherein at least one of the polycationic substance or the polyanionic substance is a bioabsorbable polymer.

9. A medical adhesive which comprises laminated films of a polyion complex according to claim 1.

10. A medical adhesive according to claim 9, wherein each film of said laminate is composed of said polyion complex.

11. A medical adhesive according to claim 1, consisting essentially of a film of said polyion complex.

12. A medical adhesive according to claim 1, consisting of a film of said polyion complex.

13. A method for bonding the tissues of a living body which comprises adhering to the affected part, a film of a polyion complex according to claim 1.

14. A method of producing a medical adhesive according to claim 1, which comprises mixing a solution of polycationic substance and a solution of a polyanionic substance to form a film of a polyion complex.

* * * * *